United States Patent
Onoda et al.

(10) Patent No.: US 10,088,459 B2
(45) Date of Patent: Oct. 2, 2018

(54) LIQUID MIXING DEVICE, AND LIQUID CHROMATOGRAPHY APPARATUS

(71) Applicant: Hitachi High-Technologies Corporation, Minato-ku, Tokyo (JP)

(72) Inventors: Yugo Onoda, Tokyo (JP); Shoji Tomida, Tokyo (JP); Kouichi Sugimoto, Tokyo (JP); Takashi Yagi, Tokyo (JP); Tetsuya Watanabe, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 15/028,492

(22) PCT Filed: Dec. 19, 2014

(86) PCT No.: PCT/JP2014/083704
§ 371 (c)(1),
(2) Date: Apr. 11, 2016

(87) PCT Pub. No.: WO2015/104976
PCT Pub. Date: Jul. 16, 2015

(65) Prior Publication Data
US 2016/0266078 A1 Sep. 15, 2016

(30) Foreign Application Priority Data
Jan. 9, 2014 (JP) .................................. 2014-002078

(51) Int. Cl.
*G01N 30/34* (2006.01)
*G01N 30/24* (2006.01)
(Continued)

(52) U.S. Cl.
CPC ............. *G01N 30/34* (2013.01); *B01D 15/12* (2013.01); *B01F 5/061* (2013.01); *B01F 5/0668* (2013.01);
(Continued)

(58) Field of Classification Search
CPC ... G01N 30/34; G01N 35/00; B01F 5/00; B01F 3/08
See application file for complete search history.

(56) References Cited

U.S. PATENT DOCUMENTS 3,045,984 A * 7/1962 Cochran ............... B01F 5/0682
138/38
3,582,048 A * 6/1971 Sarem ................... B01F 5/0644
138/38
(Continued)

FOREIGN PATENT DOCUMENTS

JP 2002-14084 A 1/2002
JP 2003-156481 A 5/2003
(Continued)

OTHER PUBLICATIONS

International Search Report (PCT/ISA/210) issued in PCT Application No. PCT/JP2014/083704 dated Mar. 24, 2015 with English-language translation (four (4) pages).
(Continued)

*Primary Examiner* — John Fitzgerald
(74) *Attorney, Agent, or Firm* — Crowell & Moring LLP

(57) ABSTRACT

A liquid-mixing device that minimizes solvent leakage and reduces creep of or damage to the component parts of said liquid-mixing device even at ultrahigh pressures of 100 MPa and up. Also, a liquid chromatography device using said liquid-mixing device. Said liquid chromatography device is provided with a supply pump that supplies a plurality of different solutions, a liquid-mixing device that mixes the
(Continued)

supplied solutions, a sample injection device that injects a sample into the mixture of solutions, a column that separates the components of the injected sample, and a detector that detects the separated components. The liquid-mixing device has an inlet-side connector through which the plurality of different solutions flow in, a liquid-mixing section in which said solutions are mixed, and an outflow-side connector through which the mixed solutions flow out. The inlet-side connector and the liquid-mixing section are directly bonded to each other via diffusion bonding, as are the liquid-mixing section and the exit-side connector.

6 Claims, 11 Drawing Sheets

(51) Int. Cl.
  *B01D 15/12*  (2006.01)
  *B01F 5/06*  (2006.01)
  *B01F 15/00*  (2006.01)
  *G01N 30/16*  (2006.01)
  *B01F 13/00*  (2006.01)
  *B81C 1/00*  (2006.01)

(52) U.S. Cl.
  CPC .... *B01F 13/0059* (2013.01); *B01F 15/00662* (2013.01); *B81C 1/00* (2013.01); *G01N 30/16* (2013.01); *G01N 30/24* (2013.01); *B01F 2005/0636* (2013.01); *B01F 2015/0009* (2013.01); *G01N 2030/347* (2013.01)

(56) References Cited

U.S. PATENT DOCUMENTS

| | | | | |
|---|---|---|---|---|
| 3,856,270 A * | 12/1974 | Hemker | ............... | B01F 5/0604 366/340 |
| 4,869,849 A * | 9/1989 | Hirose | ................. | B01F 5/0682 261/78.2 |
| 5,137,369 A * | 8/1992 | Hodan | ................. | B01F 5/0604 366/337 |
| 5,690,763 A * | 11/1997 | Ashmead | ............. | B01F 5/0604 156/252 |
| 5,887,977 A * | 3/1999 | Morikawa | ............ | B01F 5/0604 138/42 |
| 6,494,614 B1 * | 12/2002 | Bennett | ................. | B01D 61/28 210/321.84 |
| 6,923,907 B2 * | 8/2005 | Hobbs | ................. | B01F 13/0059 210/198.2 |
| 6,942,792 B2 * | 9/2005 | Aso | ..................... | B01F 13/0059 210/101 |
| 7,147,364 B2 * | 12/2006 | Oohashi | ................ | B01F 5/0256 366/162.4 |
| 7,789,108 B1 * | 9/2010 | Lawson | ............... | B01F 5/0604 138/42 |
| 7,906,016 B2 * | 3/2011 | Weber | .................... | B01J 14/005 208/267 |
| 7,909,502 B2 * | 3/2011 | Ehrfeld | ............... | B01F 5/0604 366/340 |
| 8,635,901 B2 * | 1/2014 | Adkins | .............. | G01N 30/6069 73/23.35 |
| 9,128,071 B2 * | 9/2015 | Tsukada | ................. | G01N 30/34 |
| 2004/0042340 A1 * | 3/2004 | Aso | ..................... | B01F 13/0059 366/341 |
| 2004/0252584 A1 | 12/2004 | Ji et al. | | |
| 2005/0068845 A1 * | 3/2005 | Oohashi | ................ | B01F 5/0256 366/177.1 |
| 2007/0204749 A1 * | 9/2007 | Adkins | .............. | G01N 30/6034 96/101 |
| 2010/0171055 A1 * | 7/2010 | Dourdeville | ......... | B23K 20/023 251/129.11 |
| 2011/0226040 A1 * | 9/2011 | Adkins | .............. | G01N 30/6069 73/23.39 |
| 2011/0272356 A1 | 11/2011 | Hoffmann | | |
| 2013/0014567 A1 * | 1/2013 | Bunner | ............. | B01L 3/502707 73/61.55 |
| 2013/0091933 A1 * | 4/2013 | Tsukada | ................. | G01N 30/34 73/61.55 |
| 2016/0236114 A1 * | 8/2016 | Brann | .................... | B01D 15/16 |

FOREIGN PATENT DOCUMENTS

| | | |
|---|---|---|
| JP | 2004-138413 A | 5/2004 |
| JP | 2006-281008 A | 10/2006 |
| JP | 2006-527084 A | 11/2006 |
| JP | 2013-88182 A | 5/2013 |

OTHER PUBLICATIONS

Japanese-language Written Opinion (PCT/ISA/237) issued in PCT Application No. PCT/JP2014/083704 dated Mar. 24, 2015 (five (5) pages).

Japanese-language International Preliminary Report on Patentability (PCT/IPEA/409 & PCT/IPEA/416) issued in PCT Application No. PCT/JP2014/083704 dated Oct. 13, 2015 (fifteen (15) pages).

* cited by examiner

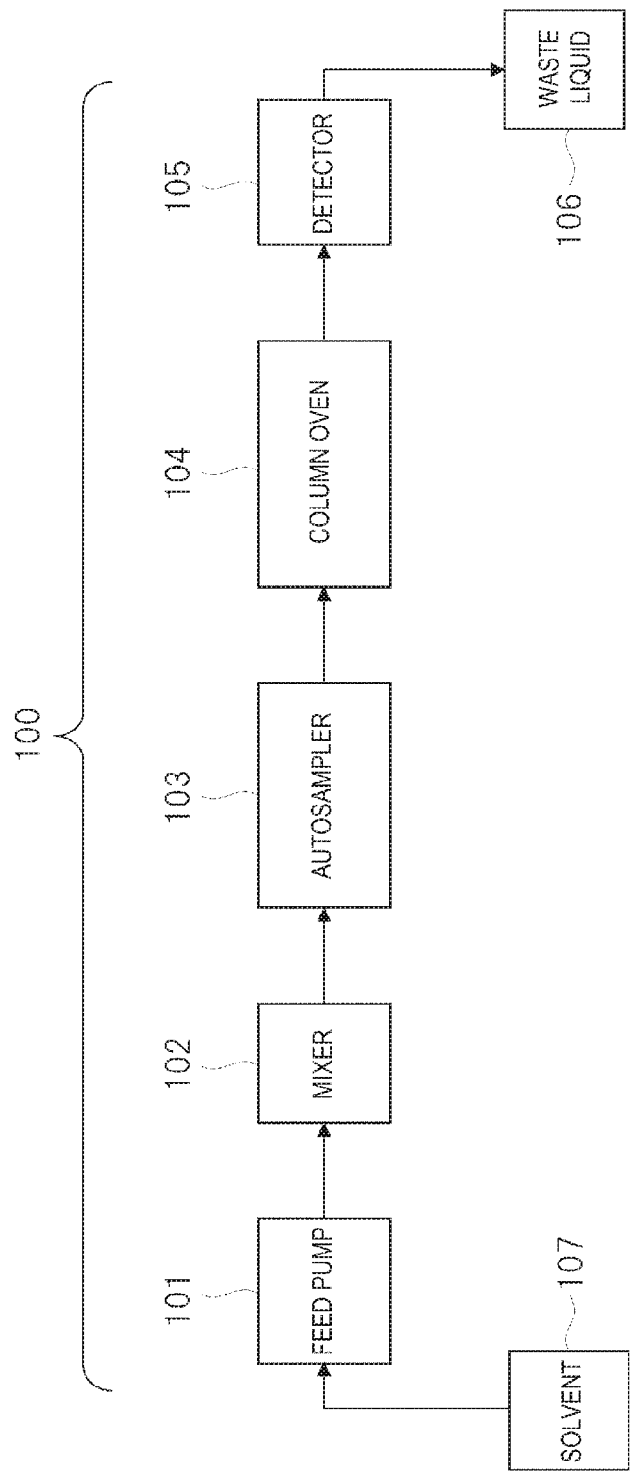
[FIG. 1]

FIG. 2C
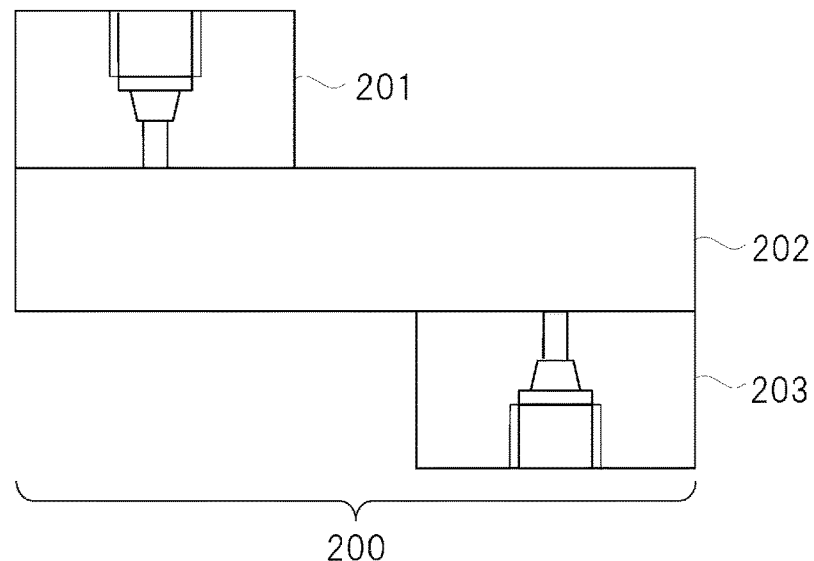
[FIG. 3] Prior Art
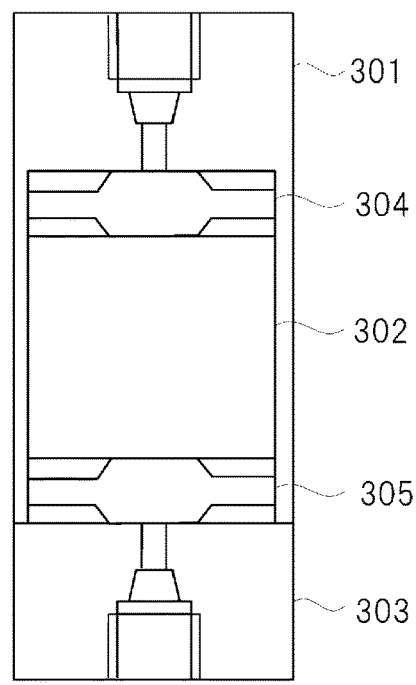

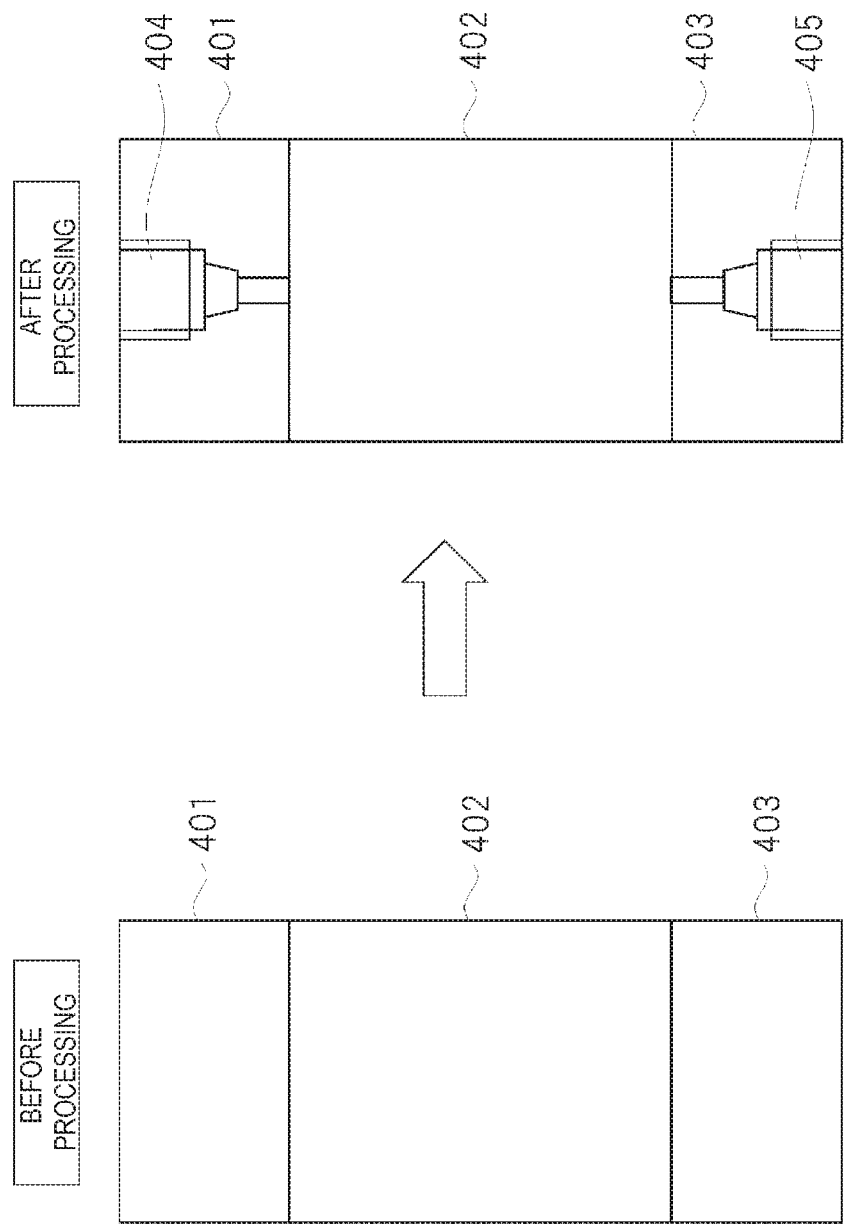

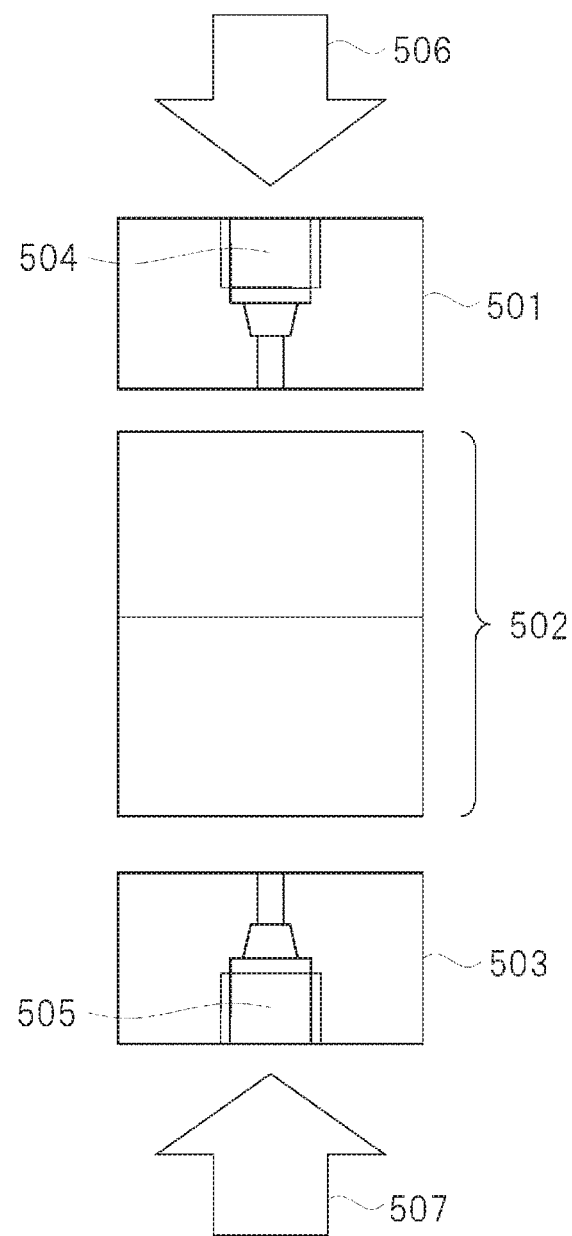
[FIG. 5]

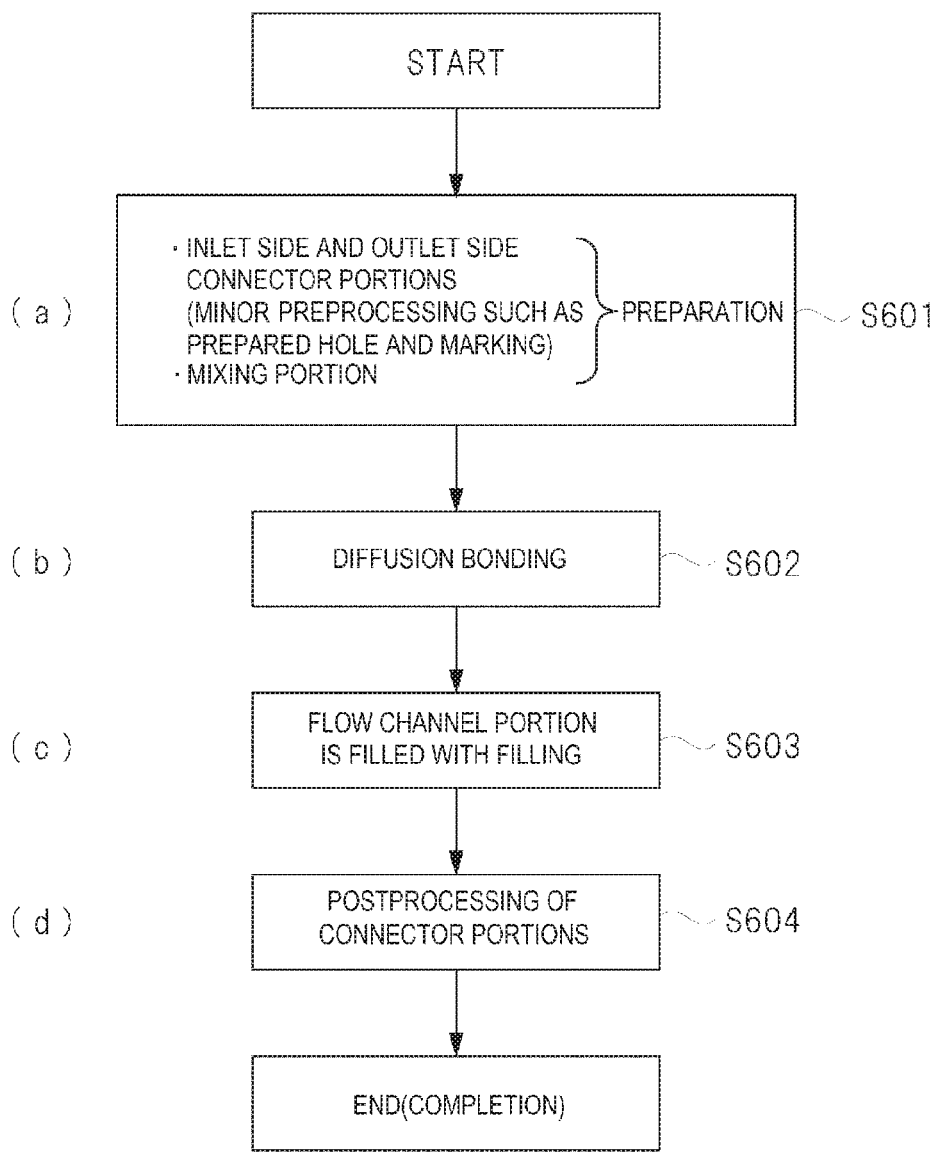

[FIG. 7]
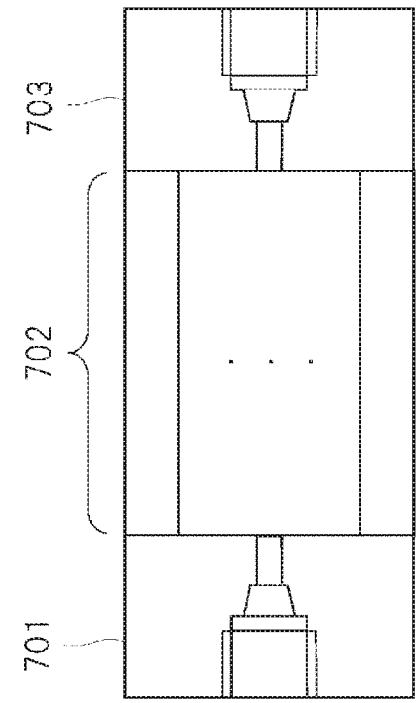
CASE WHERE LIQUID MIXING PORTION IS LAMINATED IN DIRECTION VERTICAL TO FEED DIRECTION
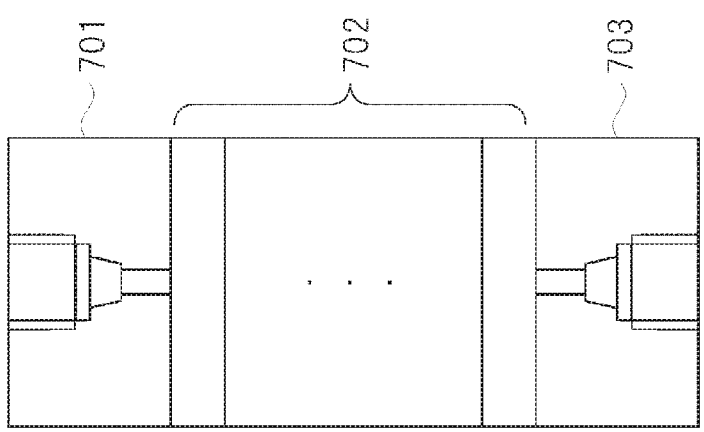
CASE WHERE LIQUID MIXING PORTION IS LAMINATED IN FEED DIRECTION

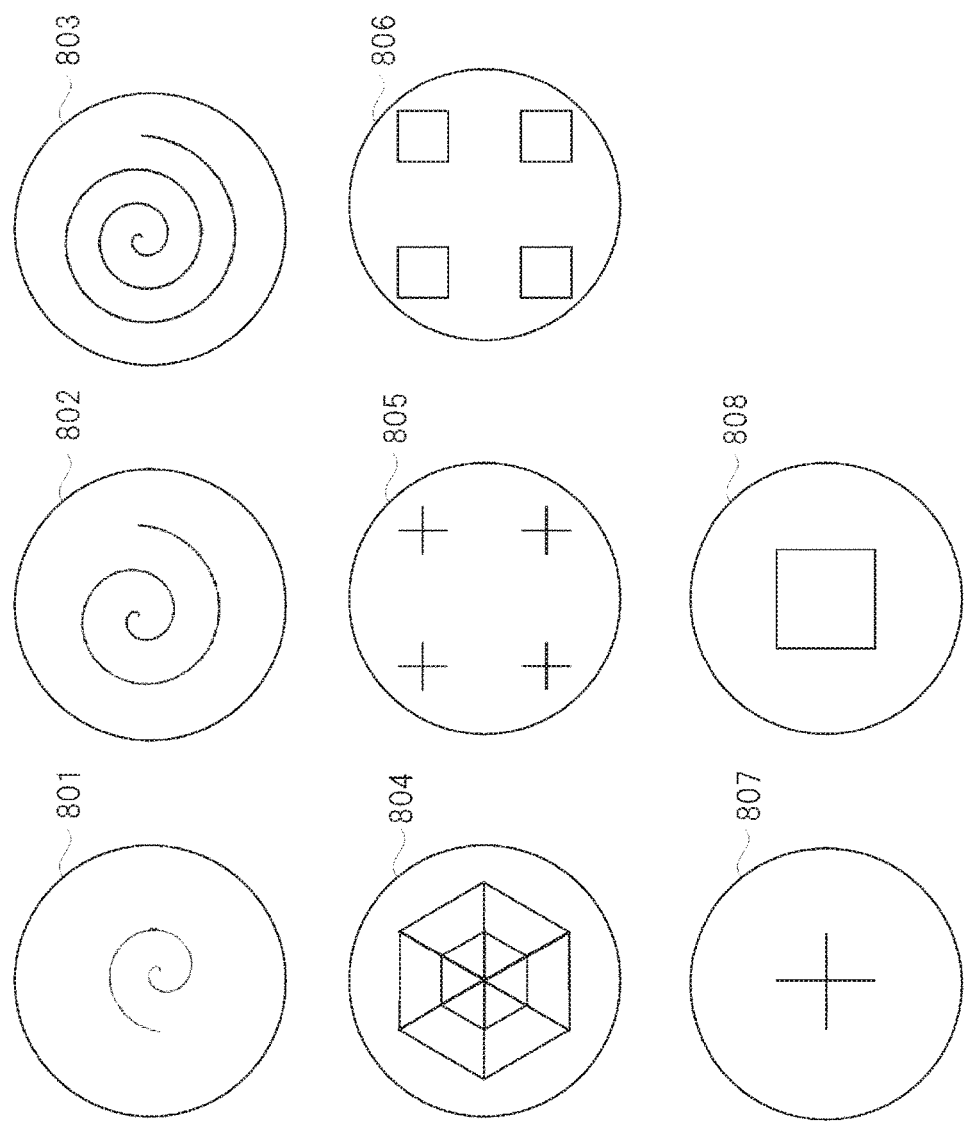

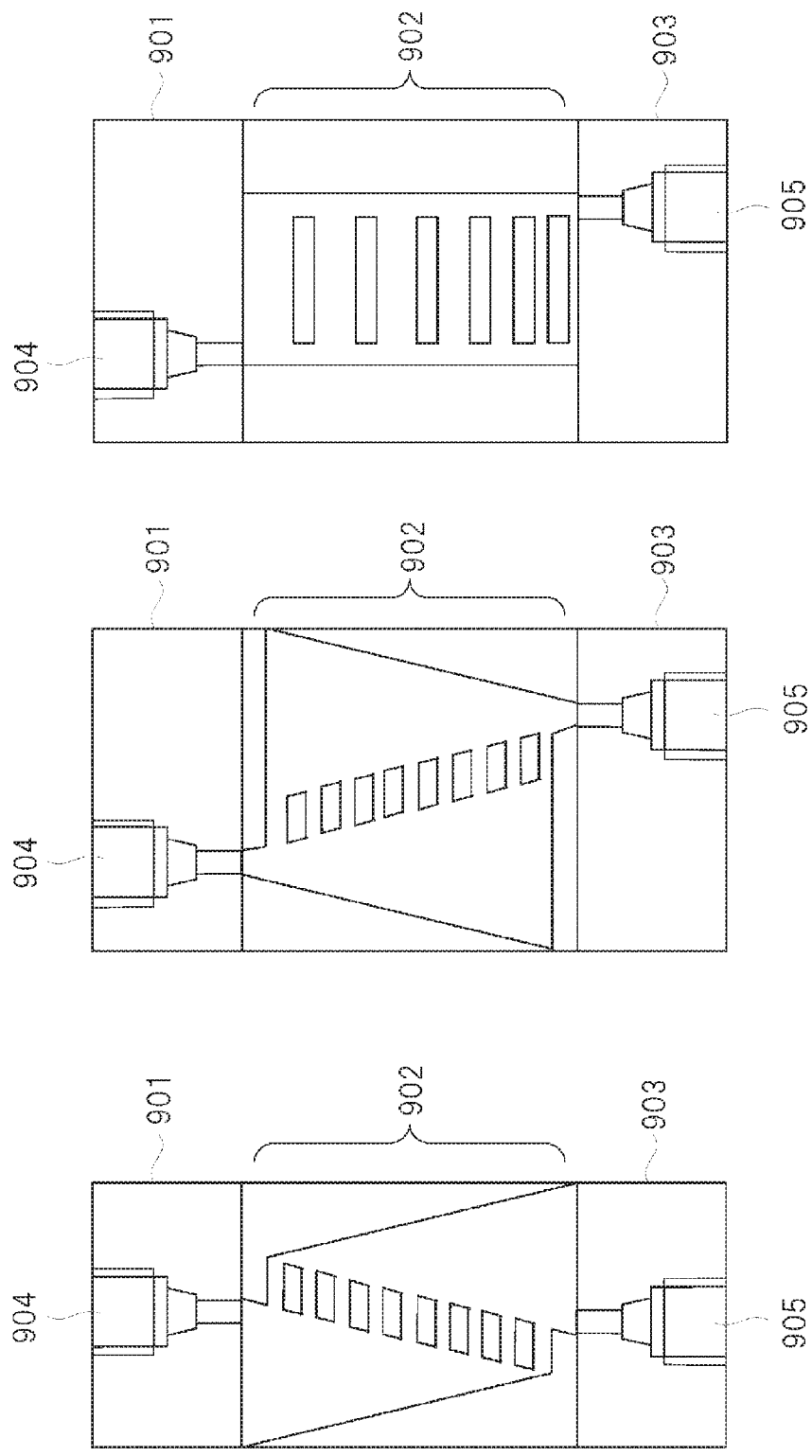
[FIG. 9]

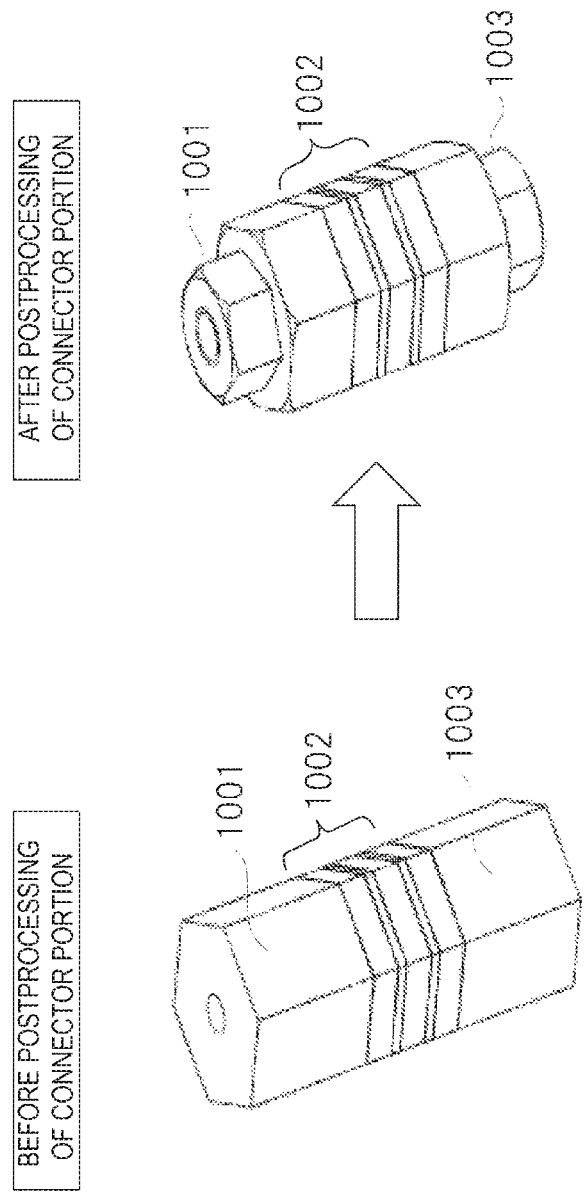
[FIG. 10]

LIQUID MIXING DEVICE, AND LIQUID CHROMATOGRAPHY APPARATUS

BACKGROUND

The present invention relates to a liquid mixing device for mixing liquids and a liquid chromatograph including the liquid mixing device.

There is PTL 1 as a technology related to the invention. PTL 1 relates to a micro mixer and discloses a configuration having a heat exchanger structure by laminating/bonding plates in which a flow channel for mixing solvents is grooved and then attaching connectors for inflow/outflow of a mixed fluid and a heat exchange medium.

BRIEF SUMMARY OF THE INVENTION

As analysis using a liquid chromatograph, there is an analysis technique in which a plurality of solvents are mixed, which is called a gradient mode. In the gradient mode, a liquid mixing device for mixing a plurality of solvents to form a mobile phase is used.

In recent years, a feed pressure of a fluid in a liquid chromatography apparatus has been increased in accordance with increase in speed of analysis and improvement in separation. In particular, an ultra high performance liquid chromatography analysis apparatus feeds a liquid at a pressure higher than 100 MPa. However, in a configuration of a liquid mixing device disclosed in PTL 1, analysis performed in a severe condition such as feeding a liquid at a high pressure described above is not considered. Therefore, in particular, a constituent member attached afterward cannot withstand a high pressure, and, for example, leakage of a liquid is caused due to deformation called creep or breakage.

In a liquid mixing device for a liquid chromatograph, which has a configuration in which a member such as a resin seal packing is inserted between a connector portion connected to a pipe and a mixing portion for mixing liquids, the seal packing is deformed or falls out due to increase in pressure, which also results in leakage of a liquid in some cases.

An object of the invention is to provide a liquid mixing device that is not deformed or broken and can reduce leakage of a liquid even in a condition of a high pressure of 100 MPa or more.

An embodiment for solving the above problem is a liquid mixing device for a liquid chromatograph, including: an inlet side connector portion to which a liquid is supplied; a liquid mixing portion having a groove/trench for mixing the supplied liquid; and an outlet side connector portion from which the mixed liquid flows out, in which the inlet side connector portion and the liquid mixing portion are connected by diffusion bonding, and the outlet side connector portion and the liquid mixing portion are connected by diffusion bonding.

According to the invention, it is possible to provide a liquid mixing device for reducing creep and breakage of a constituent part and suppressing leakage of a solvent even in a condition of an ultra high pressure of 100 MPa or more and a liquid chromatography apparatus including the liquid mixing device.

Problems, configurations, and effects other than those described above will be clarified by describing the following embodiments.

BRIEF DESCRIPTION OF THE SEVERAL VIEWS OF THE DRAWINGS

FIG. 1 is a whole configuration diagram of a liquid chromatography apparatus according to an embodiment of the invention.

FIG. 2C illustrates another example of the configuration of the liquid mixing device according to the embodiment of the invention.

FIG. 3 illustrates an example (conventional example) of a liquid mixing device including a resin seal packing and the like.

FIG. 4 illustrates a state before and after manufacturing of a liquid mixing device.

FIG. 5 illustrates a problem that arises in a liquid mixing device.

FIG. 6(A) shows a flow in a liquid mixing device according to an embodiment of the invention.

FIG. 7 is a diagram for explaining pressure application according to an embodiment of the invention.

FIG. 8 illustrates examples of a groove/trench of a liquid mixing portion according to an embodiment of the invention.

FIG. 9 illustrates examples of a laminated structure of a liquid mixing portion according to an embodiment of the invention.

FIG. 10 illustrates a state of an external appearance of a liquid mixing device according to an embodiment of the invention.

DETAILED DESCRIPTION OF THE INVENTION

Figure 2A:
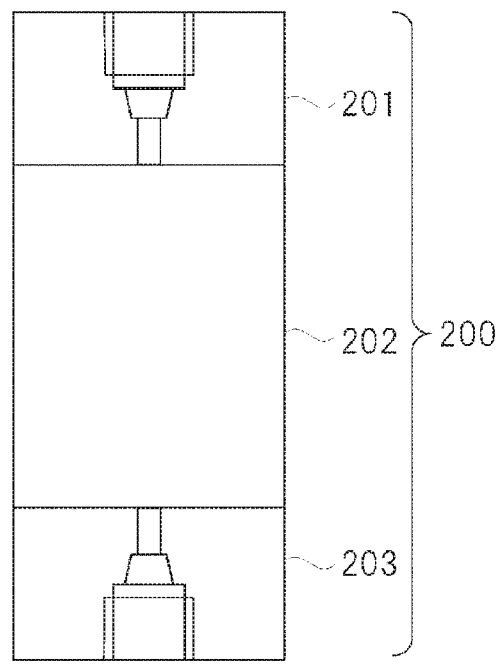
FIG. 2A illustrates an example of a configuration of a liquid mixing device according to an embodiment of the invention.

Hereinafter, embodiments of the invention will be described with reference to drawings.

FIG. 1 is a whole configuration diagram of a liquid chromatography apparatus according to an embodiment of the invention. A liquid chromatography apparatus 100 includes a feed pump 101 for feeding a solvent 107, a liquid mixing device (mixer) 102 for mixing the fed solvent, a sample injection device (autosampler) 103 for injecting a sample, a column oven 104 for keeping a separation column at a constant temperature, and a detector 105. The solvent that has passed through the detector 105 is discharged as a waste liquid 106 into a tank.

Although the liquid mixing device 102 is provided between the feed pump 101 and the sample injection device 103 in FIG. 1, the liquid mixing device 102 is also provided between the solvent 107 and the feed pump 101 in an analysis method called low-pressure gradient in some cases.

Figure 2B:
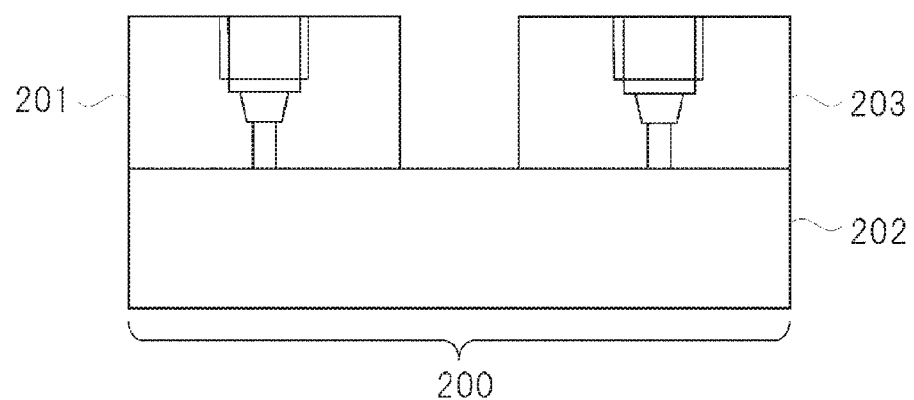
FIG. 2B illustrates another example of the configuration of the liquid mixing device according to the embodiment of the invention.

FIG. 2 illustrates a configuration of a liquid mixing device 200 according to an embodiment of the invention. The liquid mixing device 200 mainly includes an inlet side connector portion 201, a liquid mixing portion 202, and an outlet side connector portion 203. FIGS. 2(A), 2(B), and 2(C) illustrate examples of a positional relationship between the connector portions 201 and 203 and the liquid mixing portion 202. In the case where a liquid is fed in a high pressure condition, it is desirable to have a configuration (A) in which no moment is applied to the liquid mixing portion 202 and only compressive/tensile stresses act thereon.

Note that a shape of the inlet side connector portion 201 and a shape of the outlet side connector portion 203 may be the same or may be different depending on a condition of the device.

FIG. 3 illustrates a configuration example of a conventional liquid mixing device including a seal packing. In this configuration, only a liquid mixing portion 302 having a complicated flow channel shape is bonded with a bonding method such as diffusion bonding. Only in the case of the liquid mixing portion 302, it is easy to uniformly apply a pressure by using diffusion bonding or the like because the liquid mixing portion is generally configured by plane surfaces. However, because connector portions 301 and 303 are attached afterward, seal packing members 304 and 305 made of resin are generally used between the connector portions 301 and 303 and the liquid mixing portion 302. This causes necessity of retightening and a problem such as creep. Further, in order to apply a pressure to the seal packing members 304 and 305, a housing is needed in many cases, and therefore the number of constituent parts is increased, which results in high costs. Note that, although a creep amount is ignorable in a condition in which a pressure is not high (for example, 10 MPa or less), behavior as an elastic body becomes remarkable even at a room temperature in a high pressure condition (for example, 40 to 100 MPa), and therefore an influence of creep is not ignorable. A stage at which a deformation rate is high immediately after tightening is called primary creep (transient creep), and a few percent of extension generally occurs within about 10 hours. This increases a lead time in production, which is not preferable in terms of quality.

FIG. 4 illustrates a state before and after processing of a liquid mixing device according to an embodiment of the invention.

Grooves/channels 404 and 405 for connectors are not formed in an inlet side connector portion 401 and an outlet side connector portion 403, and therefore a pressure is applied thereto at the time of diffusion bonding. Thus, the inlet side connector portion 401, the outlet side connector portion 403, and a liquid mixing portion 402 can be bonded to one another. When the inlet side connector portion 401, the outlet side connector portion 403, and the quid mixing portion 402 are bonded and are then considered to be in a bulk state, thereafter of the inlet side connector portion 401 and the outlet side connector portion 403 are formed. Therefore, all parts are made of the same material such as metal including SUS, and thus a mixer is made of a material that suitably withstands a high pressure. That is, unlike the conventional structure illustrated in FIG. 3, a different material such as seal packing members does not need to be provided between the connector portions and the liquid mixing portion. Therefore, deformation, breakage, leakage of a liquid, and the like do not occur in a high pressure condition. Preparing holes and marking in grooves/channels of the inlet side connector portion 401 and the outlet side connector portion 403, does not affect diffusion bonding of the connector portions in the invention.

FIG. 5 illustrates a problem that arises in manufacturing a liquid mixing device according to another embodiment. In the case where grooves/channels 504 and 505 for connectors are manufactured before bonding, a pressure is riot applied to parts immediately below the connectors, i.e., the formed hollows, as compared with another region. Therefore, those parts are not subjected to diffusion bonding, and, because pressing is performed with several tons of force in the diffusion bonding, a region other than the hollows is slightly deformed by the diffusion bonding. Because of this slight deformation, in the case where a whole flow channel is formed in particular, a relationship between a female thread and a male thread cannot be secured in terms of connection with a pipe. There is another method in which a deformation amount is estimated in advance and then connectors are manufactured. However, in the case where a plurality of liquid mixing devices are simultaneously produced, it is difficult to have the same deformation amount in all the liquid mixing devices.

It is also considered that a liquid mixing portion 502 is prepared in advance by diffusion bonding and then only an inlet side connector portion 501 and an outlet side connector portion 503 are bonded to a mixing portion by diffusion bonding. However, bonding is performed twice or more times, which results in high costs. Therefore, such method is not preferable.

As described above, a liquid mixing device according to an embodiment of the invention is desired to be formed by the technique described with reference to FIG. 4.

Figure 6B:
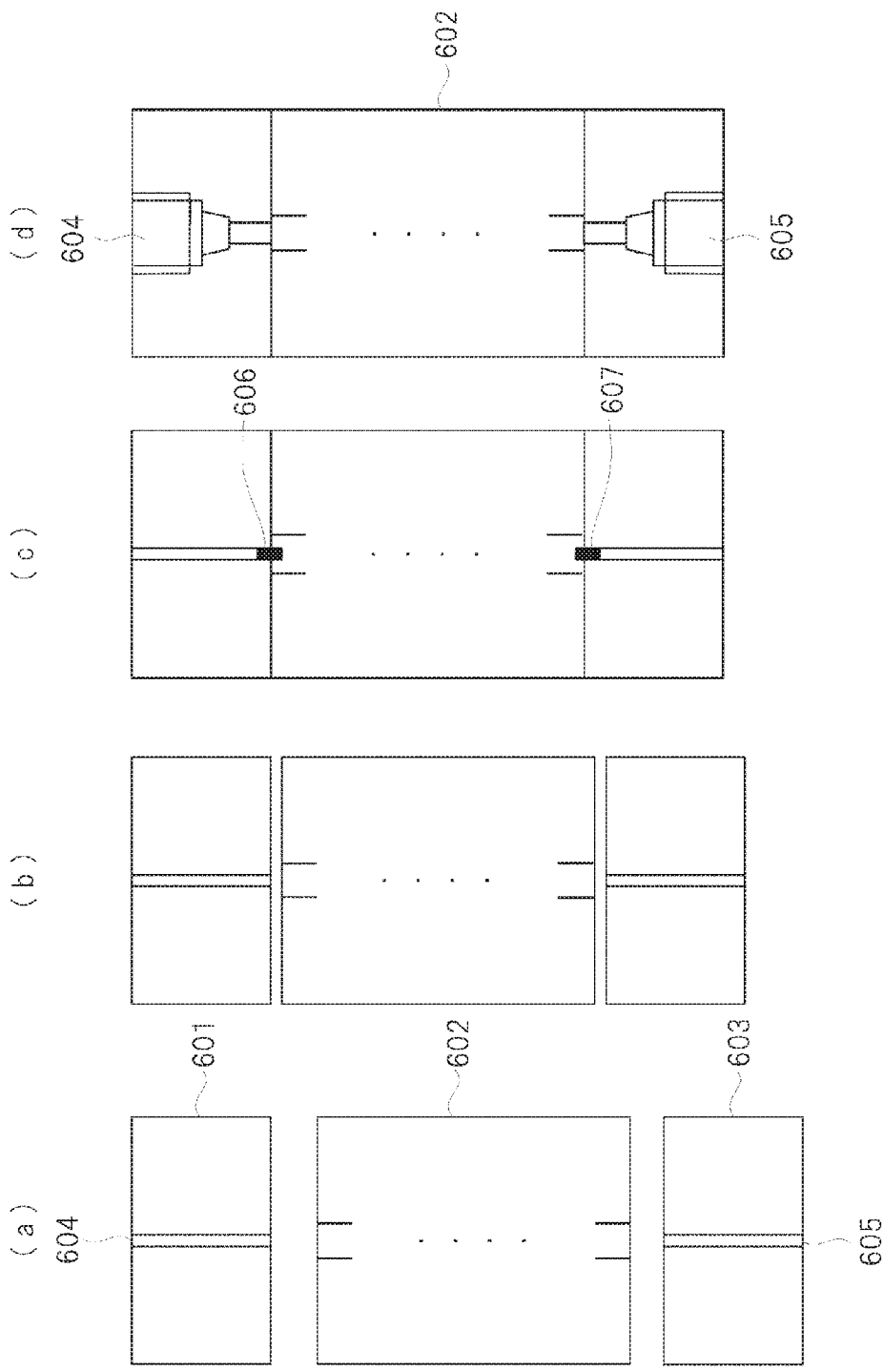
FIG. 6(B) illustrates a structure of a liquid mixing device.

FIG. 6(A) shows a flow of a liquid mixing device according to an embodiment of the invention. FIG. 6(B) illustrates a structure of a liquid mixing device.

(a) A liquid mixing portion is formed to have various complicated shapes for mixing liquids. In this step, an inlet side connector portion 601 and an outlet side connector portion 603 are manufactured and a mixing portion prepared (Step 601). Herein, manufacturing means minor manufacturing, such as grooves/channels for marking and prepared holes, is carried out in particular in upper portions of the inlet side connector portion 601 and the outlet side connector portion 603.

(b) As described above, the inlet side connector portion 601, the liquid mixing portion 602, and the outlet side connector portion 603, which have been subjected to preliminary manufacturing, are bonded to one another by diffusion bonding (Step 602).

(c) Thereafter, a flow channel of the mixing portion is filled with sealing members 606 and 607 in order to prevent entry of chip powder and cutting oil (Step 603). The sealing members 606 and 607 do not need to be special members and may be members that can temporarily block the flow channel, such as a resin material, cotton, or paper. In particular, in order to prevent entry of even a small amount of cutting oil, a fitting sealing member whose allowance is specified may be used. Further, for example, a material melted at a high temperature, such as fixture metal, can be also used. Further, in the case in which chip powder or cutting oil does not enter the flow channel of the mixing portion even when the sealing members 606 and 607 are not used, it is also possible to manufacturing without filling the flow channel with the sealing members 606 and 607.

(d) After the above manufacturing is performed, grooves/channels for connectors are formed (Step 604). A liquid mixing device formed by the above method is originally formed by diffusion bonding and therefore has an excellent pressure resistance property. No resin seal packing is used, and therefore it is unnecessary to consider occurrence of creep. The number of constituent parts is small, and therefore it is possible to suppress increase in costs.

FIG. 7 is a diagram for explaining a pressure application according to an embodiment of the invention. When a pressure is isotropically applied by using gas as a pressure medium to a liquid mixing device manufactured with the above method, in particular, a void in a liquid mixing portion 702 in which two or more layers are laminated is removed.

As illustrated in FIG. 7, a lamination direction of the liquid mixing portion 702 may be in parallel to or vertical to a feed direction.

FIG. 8 illustrates examples of a groove shape of a liquid mixing portion according to an embodiment of the invention. As illustrated in FIG. 8, it is possible to combine substrate-like members having different groove shapes 801 to 808 (spiral, spider-web, plus sign(s), square(s)) as appropriate in accordance with an analysis condition or the like to thereby laminate the members. Mixing of a plurality of kinds of liquids is promoted by causing the liquids to pass through grooves having different shapes.

FIG. 9 illustrates examples of a laminated structure of a liquid mixing portion according to an embodiment of the invention. Grooves/channels 904 and 905 for connectors may be formed at the center of an inlet side connector portion 901 and an outlet side connector portion 903 as illustrated in FIG. 9 or may be formed in end portions thereof in accordance with a laminated structure of a liquid mixing portion 902.

FIG. 10 illustrates a state of an external appearance of a liquid mixing device according to an embodiment of the invention. As illustrated in FIG. 10, connector shapes are formed in a state in which an inlet side connector portion 1001, a liquid mixing portion 1002, and an outlet side connector portion 1003 are bonded to one another by the above diffusion bonding. In this way, it is possible to provide a highly reliable liquid mixing device that has high pressure resistance and does not cause leakage of a liquid even in a high pressure condition in analysis using a liquid chromatograph.

Note that the invention is not limited to the above examples and includes various modification examples. For example, the above examples have been described in detail to easily understand the invention, and therefore the invention is not necessarily limited to the examples having all the configurations described above. Further, a part of a configuration of a certain example can be replaced with a configuration of another example, and a configuration of another example can be added to a configuration of a certain example. Further, a configuration of another example can be added to, removed from, or replaced with a part of the configuration of each example.

REFERENCE SIGNS LIST

100 . . . liquid chromatography apparatus
101 . . . feed pump
102, 200 . . . liquid mixing device (mixer)
103 . . . sample injection device (autosampler)
104 . . . column oven
105 . . . detector
106 . . . waste liquid
107 . . . solvent
201, 301, 401, 501, 601, 701, 901, 1001 . . . inlet side connector portion
202, 302, 402, 502, 602, 702, 902, 1002 . . . liquid mixing portion
203, 303, 403, 503, 603, 703, 903, 1003 . . . outlet side connector portion
304, 305 . . . seal packing member
404, 405, 504, 505, 604, 605, 904, 905 . . . groove/channel
606, 607 . . . sealing member
801-808 . . . groove/channel

The invention claimed is:

1. A liquid chromatography apparatus, comprising:
a feed pump configured to feed a plurality of solutions;
a liquid mixing device configured to mix the solutions fed by the feed pump;
a sample injection device configured to inject a sample in the solutions mixed in the liquid mixing device;
a column configured to separate components of the sample injected by the sample injection device; and
a detector configured to detect the components separated in the column, wherein:
the liquid mixing device includes an inlet side connector portion having, on a first axial end thereof, a first hollow shape that allows a first pipe to be connected to the feed pump so that the plurality of solutions fed by the feed pump flow into the inlet side connector portion, a liquid mixing portion configured to mix the solutions that have flowed into the inlet side connector portion, and an outlet side connector portion having, on a first axial end thereof, a second hollow shape that allows a second pipe to be connected to the sample injection device so that the solutions mixed in the liquid mixing portion flow into the sample injection device;
a second axial end of the inlet side connector portion that is opposite to the first axial end of the inlet side connector portion is directly diffusion bonded to the liquid mixing portion;
a second axial end of the outlet side connector portion that is opposite to the first axial end of the outlet side connector portion is directly diffusion bonded to the liquid mixing portion,
the first hollow shape and the second hollow shape are disposed on opposite sides of an imaginary line passing through a center of the inlet side connector portion and the outlet side connector portion,
the liquid mixing portion includes a plurality of laminated structures arranged one behind the other from a region of the liquid mixing portion adjacent to the first hollow shape to a region of the liquid mixing portion adjacent to the second hollow shape, and
a groove shape of the liquid mixing portion includes a spider-web shape and at least another shape selected from the group consisting of a swirl, a plus sign, and a square.

2. The liquid chromatography apparatus according to claim 1, wherein:
a third hollow shape is provided on the second axial end of the inlet side connector portion; and
a fourth hollow shape is provided on the second axial end of the outlet side connector portion.

3. A liquid chromatography apparatus, comprising:
a liquid mixing device configured to mix a plurality of solutions;
a feed pump configured to feed the solutions mixed in the liquid mixing device;
a sample injection device configured to inject a sample in the solutions fed by the feed pump;
a column configured to separate components of the sample injected by the sample injection device; and
a detector configured to detect the components separated in the column, wherein:
the liquid mixing device includes an inlet side connector portion having, on a first axial end thereof, a first hollow shape that allows a first pipe to be connected to the plurality of solutions so that the plurality of solutions flow into the inlet side connector portion, a liquid mixing portion configured to mix the solutions that have flowed into the inlet side connector portion, and an outlet side connector portion having, on a first axial end thereof, a second hollow shape that allows a second pipe to be connected to the feed pump so that the solutions mixed in the liquid mixing portion flow into the feed pump;

a second axial end of the inlet side connector portion that is opposite to the first axial end of the inlet side connector portion is directly diffusion bonded to the liquid mixing portion;

a second axial end of the outlet side connector portion that is opposite to the first axial end of the outlet side connector portion is directly diffusion bonded to the liquid mixing portion, the first hollow shape and the second hollow shape are disposed on opposite sides of an imaginary line passing through a center of the inlet side connector portion and the outlet side connector portion, the liquid mixing portion includes a plurality of laminated structures arranged one behind the other from a region of the liquid mixing portion adjacent to the first hollow shape to a region of the liquid mixing portion adjacent to the second hollow shape, and a groove shape of the liquid mixing portion includes a spider-web shape and at least another shape selected from the group consisting of a swirl, a plus sign, and a square.

4. The liquid chromatography apparatus according to claim 3, wherein:

a third hollow shape is provided on the second axial end of the inlet side connector portion; and a fourth hollow shape is provided on the second axial end of the outlet side connector portion.

5. A liquid mixing device for a liquid chromatography apparatus, comprising:

an inlet side connector portion having, on a first axial end thereof, a first hollow shape configured to connect a first pipe so that the plurality of solutions flow into the inlet side connector portion;

a liquid mixing portion configured to mix the solutions that have flowed into the inlet side connector portion; and an outlet side connector portion having, on a first axial end thereof, a second hollow shape configured to connect a second pipe so that the solutions mixed in the liquid mixing portion flow downstream, wherein a second axial end of the inlet side connector portion that is opposite to the first axial end of the inlet side connector portion is directly diffusion bonded to the liquid mixing portion, a second axial end of the outlet side connector portion that is opposite to the first axial end of the outlet side connector portion is directly diffusion bonded to the liquid mixing portion, the first hollow shape and the second hollow shape are disposed on opposite sides of an imaginary line passing through a center of the inlet side connector portion and the outlet side connector portion, the liquid mixing portion includes a plurality of laminated structures arranged one behind the other from a region of the liquid mixing portion adjacent to the first hollow shape to a region of the liquid mixing portion adjacent to the second hollow shape, and a groove shape of the liquid mixing portion includes a spider-web shape and at least another shape selected from the group consisting of a swirl, a plus sign, and a square.

6. The liquid mixing device according to claim 5, wherein a third hollow shape is provided on the second axial end of the inlet side connector portion; and a fourth hollow shape is provided on the second axial end of the outlet side connector portion.

* * * * *